United States Patent
Eisch et al.

(12)

(10) Patent No.: US 6,743,872 B1
(45) Date of Patent: Jun. 1, 2004

(54) CATALYST SYSTEMS FOR THE POLYMERIZATION OF OLEFINS AND THE STEREOREGULAR POLYMERIZATION OF ALPHA-OLEFINS VIA METALLACYCLIC INTERMEDIATES

(75) Inventors: John J. Eisch, Vestal, NY (US); John N. Gitua, Binghamton, NY (US)

(73) Assignee: The Research Foundation of the State University of New York, Albany, NY (US)

( * ) Notice: Subject to any disclaimer, the term of this patent is extended or adjusted under 35 U.S.C. 154(b) by 0 days.

(21) Appl. No.: 10/321,147

(22) Filed: Dec. 18, 2002

Related U.S. Application Data

(60) Provisional application No. 60/400,639, filed on Aug. 5, 2002.

(51) Int. Cl.$^7$ .............................. B01J 31/22; C08F 4/76
(52) U.S. Cl. ...................................... 526/170; 502/152
(58) Field of Search ........................... 502/152; 526/170

(56) References Cited

PUBLICATIONS

Cohen et al., "Structure and Reactivity of Bis(pentamethylcyclopentadienyl)(ethylene)titanium(II), a Simple Olefin Adduct of Titanium", J. Am. Chem. Soc. 1983, 105:1136–1143.*

Steigerwald et al., "Dichlorotitanacyclopropane. The Structure and Reactivity of a Metallacyclopropane", J. Am. Chem. Soc. Sep., 1985, 107, 5027–5035.*

\* cited by examiner

*Primary Examiner*—Caixia Lu
(74) *Attorney, Agent, or Firm*—Mark Levy & Associates

(57) ABSTRACT

A novel family of olefin polymerization catalysts comprising three-membered titanacarbocycles is described and illustrated. The titanacarbocycles can be readily synthesized by utilizing di-n-butyltitanium dichloride or di-t-butyltitanium dichloride at −78° C. in alkane, cycloalkane, or aromatic hydrocarbon media. These catalysts exhibit sufficient stability after their preparation that they undergo a remarkable, unprecedented reaction whereby the titanium dichloride moiety is efficiently transferred to a substrate like diphenylacetylene, ethylene, or similar compounds in order to generate the three-membered titanacarbocycles.

12 Claims, No Drawings

CATALYST SYSTEMS FOR THE POLYMERIZATION OF OLEFINS AND THE STEREOREGULAR POLYMERIZATION OF ALPHA-OLEFINS VIA METALLACYCLIC INTERMEDIATES

RELATED APPLICATION

This application claims priority from U.S. Provisional Patent Application Ser. No. 60/400,639, filed Aug. 5, 2002.

FIELD OF THE INVENTION

The present invention relates to processes for preparing olefin catalysts and, more particularly, to a method of synthesizing a novel class of alpha-olefin polymerization catalysts comprising titanacarbocycles.

BACKGROUND OF THE INVENTION

The combination of metal alkyls of Groups 1, 2 or 13 metals of the Periodic Table with metal halides, or salts of Groups 4 or 5 metals at ambient temperatures in hydrocarbon media, has long been known to function as an effective catalyst system for the polymerization of olefins, conjugated dienes, or acetylenes. These catalysts were discovered and reported by Karl Ziegler and coworkers in 1952. The resulting catalysts formed in a heterogeneous phase are further capable of the stereoregular polymerization of alpha-olefins, 1, 3-alkadienes and alkynes, as was observed and reported by Giulio Natta and coworkers in 1953. The revolutionary impact that these dual discoveries exerted on the polymer industry worldwide has been evident in the thousands of patents issued in the last 50 years that describe so-called Ziegler-Natta technology and in the joint conferral of the Nobel Prize in Chemistry on these two pioneers in 1963. An admirably thorough review of the scientific and patent literature of Ziegler-Natta polymerization technology before 1978 has been published (J. Boor, Jr., *Ziegler-Natta Catalysts and Polymerizations*, Academic Press, New York, 1979).

The specific interaction of either lithium alkyls (RLi) or aluminum alkyls ($R_3Al$) at room temperature with titanium (IV) chloride can lead to the exchange of one or two chloro ligands of $TiCl_4$ (1) for alkyl groups of RLi (Eqs. 1 and 2) to yield alkyltitanium derivatives 2 and 3:

$$TiCl_4 + RLi \longrightarrow R\text{—}TiCl_3 + LiCl \quad (1)$$
$$\phantom{TiCl_4}1 \phantom{+ RLi \longrightarrow} 2$$

$$TiCl_4 + 2\,RLi \longrightarrow R_2TiCl_2 + 2\,LiCl \quad (2)$$
$$\phantom{TiCl_4}1 \phantom{+ 2\,RLi \longrightarrow} 3$$

The polymerizing action of the heterogeneous reaction mixture of $TiCl_4$ and RLi has been ascribed either to compounds 2 and 3, which precipitate from the reaction mixture along with the by-product LiCl, and/or to the $TiCl_3$ (4) or $TiCl_2$ (5) generated by the homolyses of 2 and 3 (Eqs. 3 and 4).

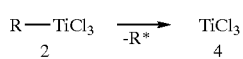

$$R\text{—}TiCl_3 \xrightarrow{-R^*} TiCl_3 \quad (3)$$
$$\phantom{R\text{—}}2 \phantom{\xrightarrow{-R^*}} 4$$

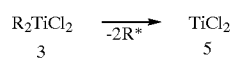

$$R_2TiCl_2 \xrightarrow{-2R^*} TiCl_2 \quad (4)$$
$$\phantom{R_2}3 \phantom{\xrightarrow{-2R^*}} 5$$

Many studies and patents corroborate that preformed $TiCl_3$, combined with a main-group metal alkyl activator, and preformed $TiCl_2$, with or without a metal alkyl activator, can effect the polymerization of ethylene and of alpha-olefins, as well as the isotactic polymerization of alpha-olefins. All such polymerizations apparently occur in a heterogeneous phase and are proposed to ensue by repeated insertions of the olefin monomer (7) into a preexisting carbon-titanium bond (e.g., 6), where the oxidation state of the titanium, n, could be 2, 3 or 4 (Eq. 5).

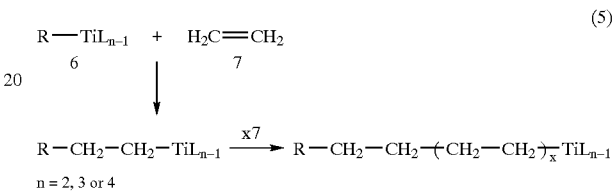

$$R\text{—}TiL_{n-1} + H_2C\text{=}CH_2 \quad (5)$$
$$\phantom{R\text{—}Ti}6 \phantom{+ H_2C\text{=}C}7$$

$$R\text{—}CH_2\text{—}CH_2\text{—}TiL_{n-1} \xrightarrow{x7} R\text{—}CH_2\text{—}CH_2\text{—}(CH_2\text{—}CH_2)_{\overline{x}}TiL_{n-1}$$
$$n = 2, 3\ or\ 4$$

In light of the novel catalyst system described herein, it is important to note that a hydrocarbon solution of titanium (IV) chloride (in alkane or arene medium), when treated at room temperature with 2 equivalents of n-butyllithium (cf. Eq. 2) immediately takes on a brown color and over a period of an hour rapidly darkens as a black solid precipitates. Finally, the supernatant liquid is colorless, and solid $TiCl_2$ and LiCl have formed quantitatively, as analyses have shown (Eq. 6). Thus any intermediate, such as di-n-butyltitanium

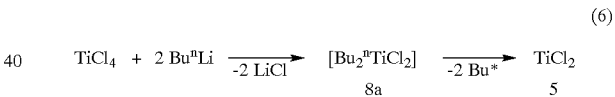

$$TiCl_4 + 2\,Bu^nLi \xrightarrow{-2\,LiCl} [Bu_2^nTiCl_2] \xrightarrow{-2\,Bu^*} TiCl_2 \quad (6)$$
$$\phantom{TiCl_4 + 2\,Bu^nLi \xrightarrow{-2\,LiCl}}\phantom{[}8a\phantom{]} \phantom{\xrightarrow{-2\,Bu^*}}5$$

dichloride 8a has completely decomposed to 5 under these conditions. With reference to the works of Friedlander and Oita, who polymerized ethylene (*Ind. Eng. Chem.*, 49, 1885 (1957)), and of Max Frankel and coworkers, who polymerized ethylene and propylene (*J. Polymer Sci.*, 28, 387 (1958) and 40, 149 (1959)) by forming their catalyst by combining various ratios of $TiCl_4$ and BuLi at ambient temperatures, it is most likely that what was actually being generated was either $TiCl_2$ or $TiCl_3$ as the active catalysts, and not 8a. Moreover, these previous workers generally prepared their catalysts and conducted their polymerizations at room temperature and under an atmosphere of nitrogen gas. Our laboratory has now shown that catalysts such as 8a are not stable at 25° C. under nitrogen but are destroyed by the nitrogen, ultimately reducing the nitrogen to ammonia. Of necessity, therefore we prepare catalyst 8a and 8b at −78° C. and under an argon atmosphere.

The present invention describes the synthesis of a novel family of olefin polymerization catalysts that can be readily generated by the preparation and utilization of di-n-butyltitanium dichloride (8a) or di-t-butyltitanium dichloride (8b), that are generated as a suspension with LiCl at −78° C. in alkane, cycloalkane, or aromatic hydrocarbon media (Eq. 7).

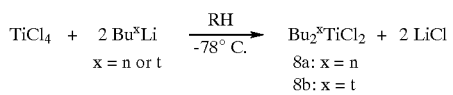

(7)

Under these conditions, 8 is sufficiently stable to undergo a remarkable, unprecedented reaction whereby the TiCl$_2$-moiety of 8 is efficiently transferred to a substrate like diphenylacetylene (9), to generate three-membered titanacycle 10 (Eq. 8), most likely via the octahedral transition state 11.

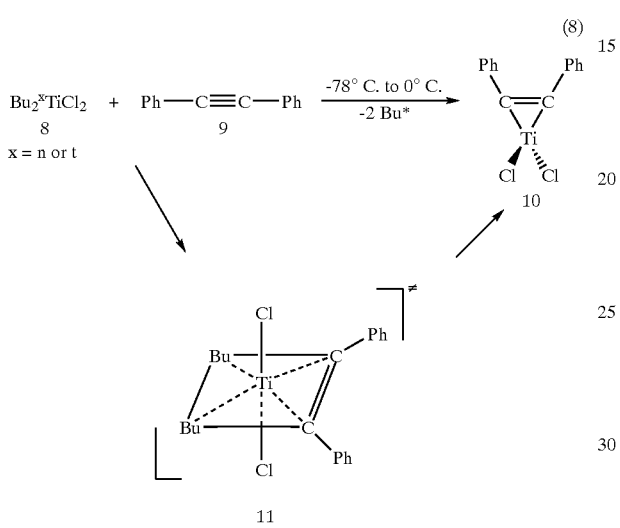

(8)

Similar reactions will be discussed hereinafter with reference to intermediates comprising such titanacyclopropanes or titanacyclopropenes. These olefin catalysts comprise a class of. three-membered titanacarbocycles, which have high activity and stereoregularity in olefin polymerization, and can be easily prepared from di-n-butyltitanium dichloride or di-t-butyltitanium dichloride when combined with either olefins or acetylenes through a novel process termed epimetalation-by-transfer and exemplified in Eq. 8.

Some advantages of synthesizing and using these novel catalysts are the following: they are relatively inexpensive to synthesize because they can be generated from commercially readily available starting materials; their synthesis is straightforward because the catalyst preparation uses common laboratory or pilot-plant apparatus; the structure of the specific catalyst can be varied widely by changing the nature of the specific acetylene, olefin or diolefin employed; polymerization proceeds with acceptable reaction rates, even at lower temperatures and pressures; polymerization of alpha-olefins may be made to proceed in an isotactic manner; and the inventive catalyst system can be employed for the copolymerization of two or more olefin monomers.

The only possible disadvantage of the present inventive catalysts is their sensitivity to traces of moisture and active-hydrogen organic compounds like alcohols, acids, 1-alkynes and to oxygen, or peroxides, all of which can destroy the carbon-titanium bond and thereby inactivate the catalyst. However, such chemical sensitivities are shared with other Ziegler-Natta polymerization catalysts as well.

Titanacycles are the key polymerization intermediates formed when a dibutyltitanium dichloride (8a or 8b) is generated by mixing titanium tetrachloride and butyllithium together (Eq. 7), then exposing them to either ethylene or propylene gas. Such titanacycles, in hexane or toluene solution, but in the absence of THF, initiate the polymerization of ethylene into polyethylene and of propylene into isotactic polypropylene.

DISCUSSION OF RELATED ART

To the best of present knowledge and belief, polymerization catalysts for olefins and other related compounds having titanacycles as an essential part of their structure have not been previously reported.

SUMMARY OF THE INVENTION

In accordance with the present invention, a novel family of olefin polymerization catalysts comprising three-membered titanacarbocycles is illustrated. The titanacarbocycles can be readily synthesized by utilizing di-n-butyltitanium dichloride or di-t-butyltitanium dichloride, prepared at −78° C. in alkane, cycloalkane, or aromatic hydrocarbon media. These procatalysts exhibit sufficient stability below 0° C. that they can undergo a remarkable, unprecedented reaction whereby the titanium dichloride moiety is efficiently transferred to a substrate, such as ethylene, an alpha-olefin, acetylene or a mono- or disubstituted acetylene, or similar compounds, in order to generate the corresponding three-membered titanacarbocycles.

It is an object of this invention to provide a new class of olefin polymerizing catalysts.

It is another object of the present invention to provide novel polymerization catalysts for olefins that can be conveniently and inexpensively synthesized.

DESCRIPTION OF THE PREFERRED EMBODIMENT

The present invention features a novel family of olefin polymerization catalysts comprising three-membered titanacarbocycles. The titanacarbocycles can be readily synthesized by utilizing di-n-butyltitanium dichloride or di-t-butyltitanium dichloride prepared at −78° C. in alkane, cycloalkane, or aromatic hydrocarbon media. These catalysts exhibit sufficient stability after their preparation that they can undergo a remarkable, unprecedented reaction whereby the titanium dichloride moiety is efficiently transferred to a substrate like ethylene, an alpha-olefin, acetylene or a mono- or disubstituted acetylene, or similar compounds, in order to generate the three-membered titanacarbocycles of the type previously shown in Eq. 8.

The novel catalyst system in all its variants can be prepared from readily available, commercially produced starting materials by use of apparatus present in any well-equipped research laboratory or industrial pilot-plant.

The catalyst can be generated and used in the heterogeneous phase for low-pressure, low-temperature polymerization of individual olefins, copolymerization of two or more olefins and diolefins, and for the isotactic polymerization of alpha-olefins without the use of expensive and less accessible metallocene or structurally complex nonmetallocene procatalysts.

Presently, it is believed that this epimetalation-by-transfer occurs via transition state 11 (Eq. 8), in which reductive elimination of the butyl groups is induced by coordination of substance 9. Proof the structure of 10 was achieved by treatment with D$_2$O and the isolation of 12 (Eq. 9).

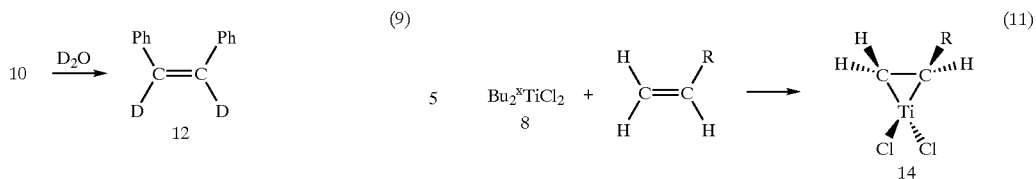

(9)

Now pertinent to this invention is the finding that suspensions of 10 in alkanes are highly active polymerization catalysts for ethylene and other olefins even at −78° C.

Similar to the behavior of diphenylacetylene (9), depicted in Eq. 8, the corresponding titanacycles like 10 can be efficiently generated from acetylenes, such as di-n-butylacetylene, bis-trimethylsilylacetylene, and methyl (phenyl)-acetylene. In addition, olefins such as the cis-isomers of 1, 2-disubstituted alkenes may also be converted to their respective titanacycles. All such titanacycles exhibit olefin polymerization activity. The simple olefins, such as ethylene, propylene, 1-hexene and styrene possess unusual potential for this novel catalyst system. Suspensions of 8 in hexane at −78° C. caused the immediate polymerization of either ethylene or propylene with the propylene being polymerized principally to isotactic polypropylene.

Owing to the unusual reactions undergone by 8 with acetylenes such as 9 and other olefins, it is reasonable to conclude the remarkable polymerization activity and stereoregulation exhibited by solutions of 8 and simple olefins is not simply due to some ill-defined interaction of the olefin monomer with the heterogeneous catalyst surface. Rather it would be logical to conclude that an epimetalation-by-transfer reaction as depicted in Eq. 8 and as illustrated for ethylene in Eq. 10 must play the key role in these polymerizations. Owing to the highly polar, strained carbon-titanium bond present in the proposed titanacycle 13, ethylene insertion into 13 and ensuing polymerization should be rapid.

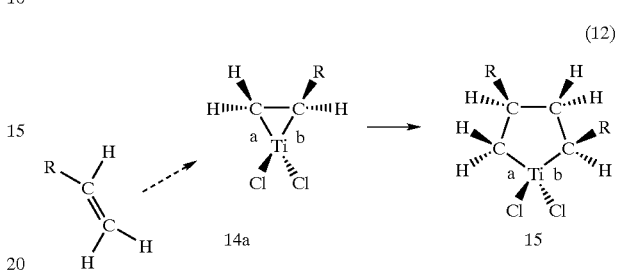

The generation of such a titanacycle in the case of propylene (14, R=Me) and other alpha-olefins (Eq. 11) would provide an excellent model for understanding the isotactic polymerization observed with these titanacyclic catalysts. For steric reasons, insertion of a second alpha-olefin (14a, shown in Eq. 12) would have the monomer approach bond a from the underside and with the R-group projecting away from the ring. Such an insertion would lead to 15 (Eq. 12). Again, for steric reasons, succeeding alpha-olefins would approach the growing ring (e.g., 15) at bond a and from the underside, leading to an isotactic ordering of the R-groups.

In order to corroborate the necessary presence and intermediacy of these three-membered titanocycles, 13 and 14, they were respectively generated by treating 8a dissolved in tetrahydrofuran (THF) with ethylene gas (Eq. 13) or with propylene gas (Eq. 14), starting at −78° C. and then warming up to 25° C. Under these the titanacyclopropanes 13 and 14 were formed but did not initiate the polymerization of the individual olefins. It is well known that various titanium(IV) Ziegler olefin polymerization catalysts are completely inactivated by stoichiometric amounts of strong Lewis bases, such as ethers or amines. It can be reasonably assumed, therefore, that in THF 13 and 14 are intermediates kinetically stabilized as bis(tetrahydrofuran) complexes, 13•2THF and 14•2THF. Because of the 1-butene formed from $Bu_2^nTiCl_2$ (8a) in the epimetalation of ethylene, considerable amounts of the 1-butene-epimetalated product (16) are also produced (Eq. 13).

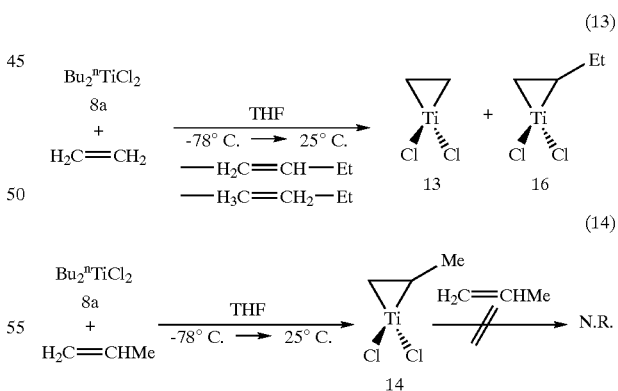

When di-t-butyltitanium dichloride (17) was employed to epimetalate ethylene in THF, intermediate 13 was formed much more efficiently and in fact underwent further insertion of ethylene to produce 18. Intermediate 18 was trapped with benzonitrile to yield valerophenone (19) upon hydrolysis (Scheme 1).

Scheme 1

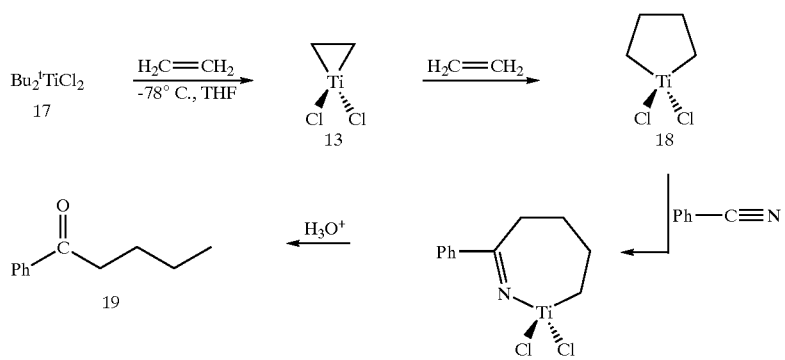

A proof of the presence of 13 in THF solution has been achieved by chemical trapping of 13 by successive reactions with benzonitrile (20) and then with carbon dioxide (22). Hydrolytic work-up and the isolation of benzoylpropanoic acid (24) is conclusive evidence that reaction intermediates 21 and 23 were involved and that the structure of the starting titanium compound must be 13 (Scheme 2). In a similar but abbreviated chemical trapping, the presence of 14 in THF solution prepared as in Eq. 14 was demonstrated by chemical trapping with benzonitrile (20), followed by hydrolysis (Scheme 3).

Scheme 2

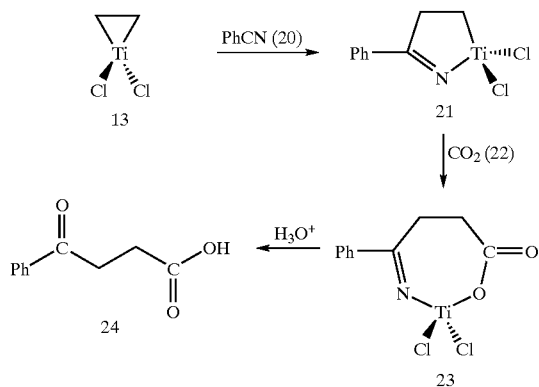

Scheme 3

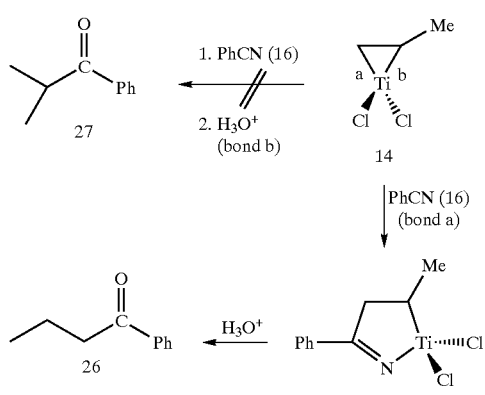

The isolation of only n-propyl phenyl ketone (26) clearly indicates that benzonitrile inserted selectively into the sterically more accessible C-Ti bond a forms 25. Insertion into the more sterically hindered C-Ti bond (b) would have resulted in the formation of isopropyl phenyl ketone (27), a product not observed.

In summary, a novel class of olefin polymerization catalysts has been disclosed, viz., three-membered titanacarbocycles exhibiting high activity and stereoregularity in hydrocarbon media, which are readily prepared from $Bu_2^nTiCl_2$ or $Bu_2^tTiCl_2$ and either olefins or acetylenes through epimetalation-by-transfer.

Since other modifications and changes varied to fit particular operating requirements and environments will be apparent to those skilled in the art, the invention is not considered limited to the examples chosen for purposes of disclosure and described below, and covers all changes and modifications which do not constitute departures from the true spirit and scope of this invention.

EXAMPLES

1. General Techniques for Catalyst Preparation and Polymerization

All operations were carried out under a dry and oxygen-free argon atmosphere employing anhydrous, freshly distilled solvents. Titanium tetrachloride, n-butyllithium and t-butyllithium (Aldrich Chemicals) were used as received. Ethylene and propylene gas (Aldrich) from the cylinders were passed through a column of Molecular Sieves before use. The $^3H$ and $^{13}C$ NMR spectra were recorded with a Bruker AM 360 MHz spectrometer ($Me_4Si$ was used as an internal standard).

2. Preparation of the Dibutyltitanium Dichlorides in Tetrahydrofuran (THF)

a) Di-n-butyltitanium Dichloride

The n-butyllithium (12.5 ml, 20 mmol, 1.6M solution in hexane) was added slowly from a gastight syringe to a stirred solution of $TiCl_4$ (1.1 ml, 10 mmol) in THF (40 ml) at −78° C. under an argon atmosphere. After the resulting mixture had stirred for 10 min. at this temperature, a red-brown reagent solution (A) had formed.

b) Di-t-butyltitanium Dichloride

A similar procedure was followed when tert-butyllithium (11.8 ml, 20 mmol, 1.7M) solution in pentane) was used to give a solution of the corresponding t-butyl reagent (B).

3. Epititanation of Ethylene in THF and Chemical Trapping of the Titanocyclic Intermediates a) Trapping with Benzonitrile 1) Reagent A Ethylene gas at 40 psi was added to the reaction solution A and the solution stirred for 30 min. at −78° C. to give a red-brown reaction mixture. Then 0.5 equivalent of benzonitrile (0.51 ml, 5 mmol) was added and the reaction mixture stirred for 0.5 h at −78° C. and then allowed to warm up to room temperature over 0.5 h period to give a dark-brown reaction mixture. After usual hydrolytic workup with 3N HCl, valerophenone (30%), ethyl phenyl ketone (2%) and α-butylbenzylamine (68%) were obtained. The ethyl phenyl ketone resulted from the chemical trapping of 13; the valerophenone and a-butylbenzylamine stemmed from the chemical trapping of both 16 and 18, the product of ethylene-insertion into 13 (Scheme 1).

2) Reagent B

To the reaction solution B, ethylene gas at 40psi was added and the solution stirred for 0.5 h at −78° C. to give a red-brown reaction mixture. Then 0.5 equivalent of benzonitrile (0.51 ml, 5 mmol) was added and the reaction mixture stirred for 0.5 h at −78° C. and then allowed to warm up to room temperature over 0.5 h period to give a dark-brown reaction mixture. After usual hydrolytic workup with 3N HCl, valerophenone (31%), ethyl phenyl ketone (53%), benzyl phenyl ketone (4%) and benzaldehyde (7%) were obtained. In this case the chemical trapping of epimetalated product 13, ethyl phenyl ketone, was much more efficient (53%). Here the valerophenone isolated arose principally from 18 because it cannot be ascribed to the epimetalated product of 1-butene, not a by-product of epimetalations with 8b. It must stem from a further insertion of ethylene into 13 to yield titanacyclopentane 18.

b) Trapping with Benzonitrile and then Carbon Dioxide

To the reaction solution A, ethylene gas at 40psi was added and the solution stirred for 0.5 h at −78° C. to give a red-brown reaction mixture. Then 0.5 equivalent of benzonitrile (0.51 ml, 5 mmol) was added and the reaction mixture stirred for 0.5 h at −78° C. and then allowed to warm up to room temperature over 0.5 h period to give a dark-brown reaction mixture. This reaction mixture was then cooled down to −78° C. and C02 gas bubbled into it for 1h. Then after 2 h at room temperature, usual hydrolytic workup with 3N HCl and addition of diethyl ether an organic extract containing the reaction products was obtained. This organic layer was separated and extracted with aqueous NaOH solution. Acidification of such aqueous extracts gave 0.20 g of liquid that was principally valeric acid (95%) with some beta-benzoylpropionic acid. These products arose from the carbonation of 18 (Scheme 1) and the sequential reactions of 13 with benzonitrile and then with $CO_2$ (Scheme 2), respectively.

4. Epititanium of Diphenylacetylene a) Tetrahydrofuran Solution

To the solution of one equivalent of $TiCl_4$ (1.1 ml, 10 mmol) and 0.5 equivalent of diphenylacetylene (0.89g, 5 mmol) in THF (40 ml) at −78° C. 2 equivalents of n-butyllithium (12.5 ml, 20 mmol, 1.6M solution in hexane) was slowly added and the resulting red-brown reaction mixture stirred at −78° C. for 1 h. The reaction mixture was then allowed to warm up to room temperature over 0.5 h followed by hydrolysis with 20 ml of $H_2O$. Extraction of the organic products was accomplished with ether anhydrous ether. cis-Stilbene (91%) and bibenzyl (0.4%) were obtained as the products.

b) Hexane Medium

1) Diphenylacetylene (0.5 Equivalent)

To the solution of TiCl4 (1.1 ml, 10 mmol) and 0.5 equivalent of diphenylacetylene (0.89 g, 5 mmol) in hexane (40 ml) at −78° C. 2 equivalents of n-butyllithium (12.5 ml, 20 mmol, 1.6M solution in hexane) was slowly added and the resulting red-brown reaction mixture stirred at −78° C. for 1 h. The reaction mixture was then allowed to warm up to room temperature over 0.5 h followed by hydrolysis with 20 ml of $H_2O$. The organic products were extracted into diethyl ether, the ether extracts dried over anhydrous $Na_2SO_4$ and the volatiles removed in vacuo. The residue consisted of cis-stilbene (85%), bibenzyl (10%) and diphenylacetylene (5%).

2) Diphenylacetylene (1.0 Equivalent)

To the yellow solution mixture of $TiCl_4$ (1.1 ml, 10 mmol) and 1 equivalent of diphenylacetylene (1.78 g, 10 mmol) in hexane (40 ml) at −78° C. were added 2 equivalents of n-butyllithium (12.5 ml, 20 mmol, 1.6M solution in hexane) and the solution stirred at −78° C. for 1 h. The dark brown reaction mixture was warmed to room temperature over 0.5 h. The reaction was quenched with 20 ml of $H_2O$ and the organic products taken up in diethyl ether. Hexaphenylbenzene (0.25 g, 14%) remained insoluble. The ether extract was found to contain 1.50 g consisting of cis-stilbene (59%), bibenzyl (4%), hexaphenylbenzene (6%) and diphenylacetylene (17%).

c) Deuteriation Labeling

In the foregoing epititanations of diphenylacetylene conducted in THF or hexane, parallel epititanations were conducted in the same manner but the hydrolytic workup in each case was performed with 3N DCl in $D_2O$. In these experiments the cis-stilbene isolated was >98% dideuteriated at the vinylic carbon atoms (12).

5. Epimetalation of Propylene and Trapping with Benzonitrile

To a solution of $TiCl_4$ (1.1 ml, 10 mmol) in THF (40 ml) at −78° C., propylene gas at 40psi was added while the solution was stirred for 10 min. at −78° C. To the resulting deep yellow reaction mixture, 2 equivalents of t-butyllithium (11.8 ml, 20 mmol, 1.7M solution in pentane) were then slowly added and the resulting reaction mixture stirred at −78° C. for 0.5 h to give a red-brown solution. Then, 0.5 equivalent of benzonitrile (0.51 ml, 5 mmol) was added and the reaction mixture stirred for 0.5 h at −78° C. and allowed to warm up to room temperature over 0.5 h period to give a dark-brown reaction mixture. After usual hydrolytic workup with 3N HCl, n-propyl phenyl ketone (72%), benzyl phenyl ketone (2%) and benzaldehyde (8%) were obtained. The n-propyl phenyl ketone is the chemical trapping product of 14, with preferential insertion of benzonitrile into bond a (Scheme 3).

6. Polymerization of Ethylene a) Procatalyst Preparation with t-Butyllithium To the light-orange solution of $TiCl_4$ (1.0 ml, 1.0 mmol, 1.0M solution in toluene) in hexane (100 mm) at −78° C., ethylene gas at 40psi was added while the solution was stirred for 5 min. at −78° C. To the resulting reaction mixture, 2 equivalents of t-butyllithium (1.18 ml, 2 mmol, 1.7M solution in pentane) were then slowly added and the resulting mixture stirred at −78° C. for 5 minutes to give a white-brown solid. The reaction mixture was quenched with 30 ml of 3N HCl and then washed with 60 ml of $H_2O$ and 50 ml of methanol. Filtration and several washes with methanol gave white, solid polyethylene, 5.5 g.

b) Procatalyst Preparation with n-Butyllithium

To the light-orange solution of $TiCl_4$ (1.0 ml, 1.0 mmol, 1.0M solution in toluene) in hexane (100 mm) at −780C., ethylene gas at 40psi was added while the solution was stirred for 5 min. at −78° C. To the resulting reaction mixture, 2 equivalents of n-butyllithium (1.25 ml, 2 mmol, 1.6M solution in hexane) were then slowly added and the resulting mixture stirred at −78° C. for 5 min. to give a white-brown solid. The reaction mixture was quenched with 30 ml of 3N HCl and then washed with 60 ml of $H_2O$ and 50 ml of methanol. Filtration and several washes with methanol gave white, solid polyethylene, 2.2 g.

C. Procatalyst Preparation with Diphenylacetylene and n-Butyllithium

To a solution of $TiCl_4$ (5 ml, 5 mmol, 1M solution in toluene) and 1 equivalent of diphenylacetylene (0.89 g, 5 mmol) in hexane (40 ml) at −78° C. was added 2 equivalents of n-butyllithium (6.25 ml, 10 mmol, 1.6M solution in hexane) and the solution stirred at −78° C. for 1 h. The dark-brown reaction mixture was warmed up to room temperature over 1 h. To this reaction mixture, ethylene gas at 40psi was added and the suspension mixture stirred for 1 h at room temperature. The reaction mixture was quenched with 30 ml of 3N HCl and then washed with 60 ml of $H_2O$ and 50 ml of methanol diethyl ether. The polymer was filtered off and washed several times with methanol until the solid was colorless. The filtrate was concentrated to give a yellow suspension =0.48 g which was found to contain cis-stilbene, bibenzyl (traces, and hexaphenylbenzene. After drying, 3.44 g of colorless polyethylene was obtained.

d. Comparison Examples of Attempted Ethylene Polymerization without $TiCl_4$

The polymerizations of ethylene described in Examples 6a and 6b were individually carried out as therein described, except that no TiCl4 was employed. In the absence of $TiCl_4$ neither experiment led to any polyethylene formation.

7. Polymerization of Propylene

To the light-orange solution of $TiCl_4$ (1.0 ml, 1.0 mmol, 1.0M solution in toluene) in hexane (100 mm) at −78° C., propylene gas at 40psi was added while the solution was stirred for 5 min. at −78° C. To the resulting reaction mixture, 2 equivalents of n-butyllithium (1.25 ml, 2 mmol, 1.6M solution in hexane) were then slowly added and the resulting reaction mixture stirred at −78° C. for 5 min. to give a white-dark brown solid. The reaction mixture was quenched with 30 ml of 3N HCl and then washed with 60 ml of $H_2O$ and 50 ml of methanol. Filtration and several washes with methanol gave a white solid, 1.20 g, which was isotactic polypropylene, as determined by consulting reference spectra. The methanol washings upon concentration gave a clear viscous liquid, 0.17 g, whose NMR spectra exhibited the signals of atactic polypropylene.

8. Polymerization of Alpha-olefins

To the yellow solution mixture of TiCl4 (1.1 ml, 10 mmol) in hexane (50 ml) at −78° C. 2 equivalents of n-butyllithium (12.5 ml, 20 mmol, 1.6M solution in hexane) was slowly added and the resulting light-brown reaction mixture of di-n-butyltitanium dichloride and lithium chloride stirred at −78° C. for 20 min. followed by the addition of the alpha-olefin. The red-dark brown reaction mixture obtained was then allowed to warm up to room temperature over 1 h to give a dark brown reaction mixture. Hydrolysis was performed with 20 ml of 3N HCl followed by extraction of the organic products with diethyl ether (3×20 ml).

| Entry | Olefin | Products | Physical state |
|---|---|---|---|
| 1 | 1-hexene (1 equiv.) | poly(1-hexene) (isotactic) | viscous liquid |
| 2 | 1-octene (1 equiv.) | poly(1-octene) + octane (traces) | light yellow viscous liquid |
| 3 | 1-decene (1 equiv.) | poly(1-decene) (atactic) + decane (traces) | light yellow viscous liquid |
| 4 | styrene (0.5 equiv.) | polystyrene (isotactic) + ethylbenzene (traces) | light yellow viscous liquid |
| 5 | 4-phenyl-1-butene (0.5 equiv.) | poly(4-phenyl-1-butene) + butylbenzene (traces) | light yellow viscous liquid |

Having thus described the invention, what is desired to be protected by Letters Patent is presented in the subsequently appended claims.

What is claimed is:

1. An olefin polymerization catalyst of high activity and stereoregularity in hydrocarbon media, comprised of a three-membered titanacarbocycle.

2. A method of synthesizing the three-membered titanacarbocycle olefin polymerization catalyst in accordance with claim 1, comprising the step of reacting a butyltitanium(IV) chloride with an olefin through an epimetalation by transfer.

3. A method of synthesizing the three-membered titanacarbocycle, olefin polymerization catalyst in accordance with claim 1, comprising the step of reacting a butyltitanium(IV) chloride with an acetylenic compound via an epimetalation-by-transfer process.

4. The method in accordance with claim 2, where the butyltitanium(IV) chloride comprises a di-n-butyltitanium (IV) chloride and a di-t-butyltitanium(IV) chloride compound.

5. The method in accordance with claim 3, where the butyltitanium(IV) chloride comprises a di-n-butyltitanium (IV) chloride and a di-t-butyltitanium(IV) chloride compound.

6. A method of synthesizing a three-membered titanacarbocycle olefin polymerization catalyst comprising the step of reacting a butyltitanium(IV) chloride compound with an olefin through an epimetalation-by-transfer process.

7. A method of synthesizing a three-membered titanacarbocycle, olefin polymerization catalyst comprising the step of reacting a butyltitanium(IV) chloride compound with an acetylene-type compound via an epimetalation-by-transfer process.

8. The method in accordance with claim 6, wherein the butyltitanium(IV) chloride comprises a di-n-butyltitanium (IV) chloride and a di-t-butyltitanium(IV) chloride compound.

9. The method in accordance with claim 7, wherein the butyltitanium(IV) chloride comprises a di-n-butyltitanium (IV) chloride and a di-t-butyltitanium(IV) chloride compound.

10. A method of polymerizing an olefin compound by reacting it with a three-membered titanacarbocycle.

11. The method of claim 10, wherein the olefin compound comprises an alpha-olefin.

12. The method of claim 10, wherein the olefin compound comprises a di-olefin.

* * * * *